(12) United States Patent
Jin et al.

(10) Patent No.: US 11,426,353 B2
(45) Date of Patent: Aug. 30, 2022

(54) COMPOSITE COATING FOR AN ACTIVE AGENT

(71) Applicant: 13400719 Canada Inc., Toronto (CA)

(72) Inventors: Ted Jin, Toronto (CA); Nana Akyaa Ackaah-Gyasi, Toronto (CA); Kuan Huan Gary Chen, Toronto (CA)

(73) Assignee: 13400719 Canada Inc., Toronto (CA)

( * ) Notice: Subject to any disclaimer, the term of this patent is extended or adjusted under 35 U.S.C. 154(b) by 0 days.

(21) Appl. No.: 17/102,036

(22) Filed: Nov. 23, 2020

(65) Prior Publication Data

US 2021/0401760 A1 Dec. 30, 2021

Related U.S. Application Data

(60) Provisional application No. 63/043,234, filed on Jun. 24, 2020.

(51) Int. Cl.
*A61K 9/48* (2006.01)

(52) U.S. Cl.
CPC .......... *A61K 9/4833* (2013.01); *A61K 9/4866* (2013.01); *A61K 9/4875* (2013.01)

(58) Field of Classification Search
CPC ... A61K 9/4833; A61K 9/4866; A61K 9/4875
See application file for complete search history.

(56) References Cited

U.S. PATENT DOCUMENTS

| | | | |
|---|---|---|---|
| 8,871,266 B2 | 10/2014 | Crittenden et al. | |
| 10,111,835 B2 | 10/2018 | Agueros Bazo et al. | |
| 10,159,650 B2 * | 12/2018 | Schad | A23G 3/343 |
| 10,188,609 B2 | 1/2019 | Tran et al. | |
| 11,039,637 B2 * | 6/2021 | Penhasi | A23P 10/30 |
| 2003/0198683 A1 * | 10/2003 | Li | A61K 9/5084 |
| | | | 424/494 |
| 2010/0310713 A1 | 12/2010 | Viebke et al. | |
| 2011/0123677 A1 | 5/2011 | Rivera et al. | |
| 2013/0251792 A1 | 9/2013 | Kowalski et al. | |
| 2013/0323362 A1 * | 12/2013 | Penhasi | A61K 9/5073 |
| | | | 426/61 |
| 2015/0086623 A1 * | 3/2015 | Chung | A61K 9/5084 |
| | | | 424/452 |
| 2015/0132380 A1 * | 5/2015 | Bravo Gonzalez | A61K 9/2886 |
| | | | 424/472 |
| 2015/0157670 A1 | 6/2015 | Kriz et al. | |
| 2015/0306038 A1 | 10/2015 | Tran et al. | |
| 2016/0360777 A1 * | 12/2016 | Penhasi | A23L 33/135 |
| 2017/0020169 A1 | 1/2017 | Rivera et al. | |
| 2017/0165201 A1 * | 6/2017 | Anselmo | A61K 35/742 |
| 2017/0273344 A1 | 9/2017 | Quintens et al. | |
| 2018/0084805 A1 | 3/2018 | Fang et al. | |
| 2019/0240163 A1 | 8/2019 | Niichel et al. | |

FOREIGN PATENT DOCUMENTS

| | | | |
|---|---|---|---|
| EP | 2868206 | 9/2014 | |
| EP | 2751254 | 12/2017 | |
| EP | 3205216 | 8/2018 | |
| WO | WO-2008016887 A2 * | 2/2008 | ............. G06Q 10/00 |
| WO | WO-2019209261 A * | 10/2019 | ........... A23K 20/163 |

OTHER PUBLICATIONS

Shi et al.—"Encapsulation of probiotic Lactobacillus bulgaricus in alginate-milk microspheres and evaluation of the survival in simulated gastrointestinal conditions"—Journal of Food Engineering 117 (2013) 99-104.

Sungthongjeene et al.—"Development of pulsatile release tablets with swelling and rupturable layers", Journal of Controlled Release 95 (2004) 147-159.

Bussemer et al.—"A pulsatile drug delivery system based on rupturable coated hard gelatin capsules", Journal of Control Release 93 (2003) 331-339.

Li et al.—"Preparation of alginate/chitosan/carboxymethyl chitosan complex microcapsules and application in Lactobacillus casei ATCC 393", Carbohydrate Polymers 83 (2011) 1479-1485.

Chavarri et al.—"Microencapsulation of a probiotic and prebiotic in alginate-chitosan capsules improves survival in simulated gastrointestinal conditions", International Journal of Food Microbiology 142 (2010) 185-189.

Lucinda-Silva et al.—"Alginate-chitosan systems: In vitro controlled release of triamcinolone and in vivo gastrointestinal transit", Carbohydrate Polymers 81 (2010) 260-268.

De Barros et al.—"A Laminated Polymer Film Formulation for Enteric Delivery of Live Vaccine and Probiotic Bacteria", Research Article—Pharmaceutical Technology, Journal of Pharmaceutical Sciences 103: 2022-2032, 2014.

D'Orazio et al.—"Micro Encapsulation of New Probiotic Formulations for Gastrointestinal Delivery in vitro Study Assess Viability and Biological Properties", Appl. Microbial Biotechnol, 2015, pp. 1-11.

* cited by examiner

Primary Examiner — Robert A Wax
Assistant Examiner — Olga V. Tcherkasskaya
(74) Attorney, Agent, or Firm — Gowling WLG (Canada) LLP

(57) ABSTRACT

Active agent encapsulated with a protective composite coating is provided. The coating comprises a first hydrophilic water-swellable inner coating comprising a sealant agent combined with a plasticizer to coat particles of the active agent; and a second hydrophobic outer coating comprising a hydrophobic component combined with an enteric polymer and a plasticizer. The composite coating enhances the stability/viability of the active agent during prolonged storage prior to administration, and on exposure to harsh physiological conditions (e.g. gastric environment) following administration to permit enteric delivery of the active agent. A method of preparing the coated active agent is also provided.

9 Claims, 2 Drawing Sheets

COMPOSITE COATING FOR AN ACTIVE AGENT

FIELD OF THE INVENTION

The present invention generally relates to encapsulating of administrable active agents, and in particular, relates to composite coatings useful for such agents.

BACKGROUND

Encapsulation of active agents, such as therapeutic, prophylactic, nutritive or diagnostic agents, is known in the art. Coatings used to encapsulate such agents are designed to protect the active agent, permit delayed release of an active agent, to facilitate administration of an active agent, to promote patient compliance, among other reasons.

Probiotics, one type of active agent, are defined as "live microorganisms, which, when administered in adequate amounts, confer a health benefit on the host" (FAO/WHO, 2002). The range of beneficial effects of probiotics includes modulation and maintenance of a healthy microbiota, inhibition of pathogens, and immunostimulation (Bohbot et al, 2018; Kim et al, 2018; Wickens et al, 2018).

In order for probiotics to be effective, the bacteria must remain viable throughout the various conditions encountered during food processing applications, as well as during storage for the duration of the shelf life of the probiotic. If the probiotics are targeting gut health, they must also survive passage through the harsh environment of the stomach prior to the intended delivery to the intestines in order to maintain efficacy. This aspect of probiotic stability and viability constitutes an economic burden for most manufacturers. This also limits the incorporation of probiotics in many product categories.

Various strategies have been employed to mitigate these challenges including isolating strains with intrinsic resistance (Son et al, 2018) and encapsulation technologies (Sarao & Arora, 2015). While rare, a few probiotic strains have also shown some activity despite being inactivated, removing the need to develop strategies for maintaining their viability (Jensen et al, 2017; Kamilya et al, 2015). However, the effects of inactivated bacteria can be vastly diminished as compared to live bacteria, limiting their application (Zimmermann et al, 2018). Furthermore, non-viable cells will not replicate rendering their benefits, if any, to be short-term. In addition, bacterial species that can be inactivated or that have intrinsic resistance are extremely limited, and most species that show ability to confer health benefits are not amongst them.

Microencapsulation of probiotic bacteria is a method of protecting the bacteria from harsh conditions. The probiotics are surrounded by a physical barrier created by a coating, or are entrapped in a microencapsulation matrix (Sarao & Arora, 2015). The majority of research relating to microencapsulation technologies has focused on safe probiotic passage through the stomach with release in the intestines. The most commonly used biopolymers for these microcapsules are alginate and chitosan. Alginate is a polymer typically obtained from seaweed, having numerous biomedical applications due to its low toxicity, low cost, and ability to undergo gelation by addition of divalent cations such as $Ca'$. Chitosan is derived from the N-deacetylation of chitin, and can form gels with sodium alginate by ionic crosslinking. Chitosan-coated alginate microencapsulation has been shown to be a suitable vehicle to allow for controlled release of viable probiotic cells in the intestines (Chávarri et al, 2010; D'Orazio et al, 2015). This encapsulation protects the cells from the acidic environment of the stomach, and once in the intestine, the increase in pH causes the deprotonation of the amino groups of chitosan, causing their detachment from the alginate core. The alginate will also dissolve due to chelation of the matrix, releasing the probiotic cells. Other materials that have shown resistance to stomach acid conditions include gellan gum, xanthan gum, and milk proteins (Sarao & Arora, 2015; Shori, 2017).

While the commonly used excipients such as alginate and chitosan in microencapsulation technology alleviates the problem associated with probiotic stability during transit to the intestines, it still does not solve the issue of maintaining probiotic cell viability during formulation in many food applications. For instance, alginate microparticles are porous, limiting their use as protectants in many food processing steps. Porous microparticles can also lead to significant reductions in shelf life of the products such as probiotics.

There remains, thus, a need for an encapsulation technology that maintains the integrity, stability and/or efficacy of an active agent prior to administration, and prior to delivery/release at a target site.

SUMMARY OF THE INVENTION

A novel polymeric composite coating for an active agent has now been developed. The coating comprises two layers, a first inner swellable layer and a second outer water-resistant protective layer, the combination of which protects the active agent from exposure to harsh conditions on administration, and also maintains the integrity and stability of the active agent during storage.

Accordingly, in one aspect, a method of encapsulating an active agent is provided comprising the steps of:

i) applying to particles of the active agent a first hydrophilic water-swellable inner coating comprising a sealant film combined with a plasticizer to form coated particles; and ii) applying to the coated particles a second water-resistant outer coating comprising a hydrophobic non-swellable component combined with an enteric polymer and a hydrophobic plasticizer.

In another aspect, active agent encapsulated with a composite coating is provided. The composite coating comprises: i) a first hydrophilic swellable inner coating comprising a sealant film combined with a plasticizer; and ii) a second water-resistant outer coating comprising a hydrophobic non-swellable component combined with an enteric polymer and a hydrophobic plasticizer.

These and other aspects of the invention are described by reference to the following Figures.

DETAILED DESCRIPTION OF THE INVENTION

Figure 1:
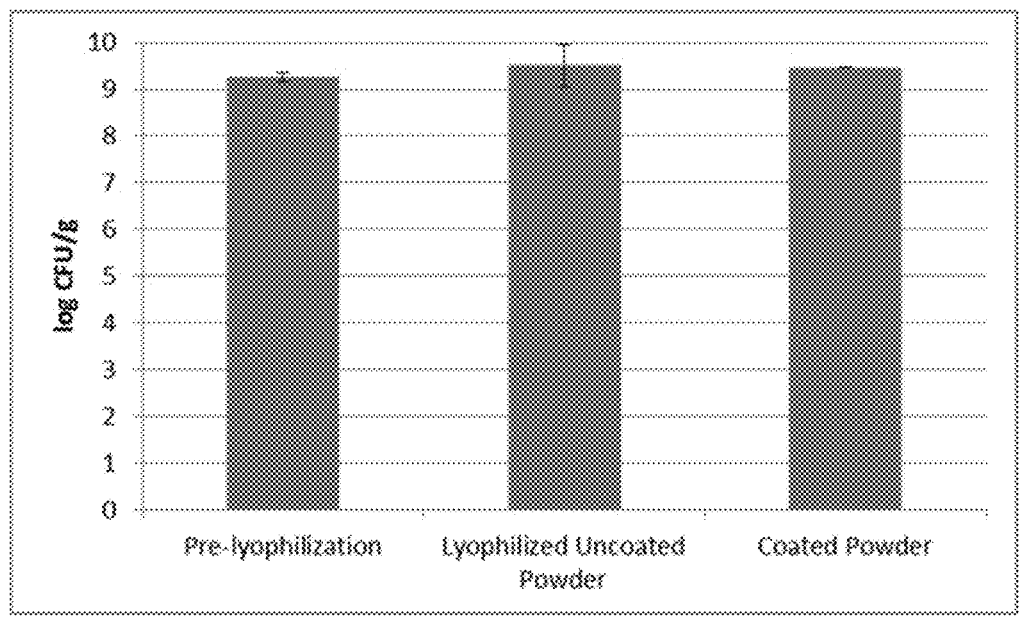
FIG. 1 graphically illustrates that probiotic cell viability was maintained following lyophilization and application of inner and outer coatings according to an embodiment of the invention.
Figure 2:
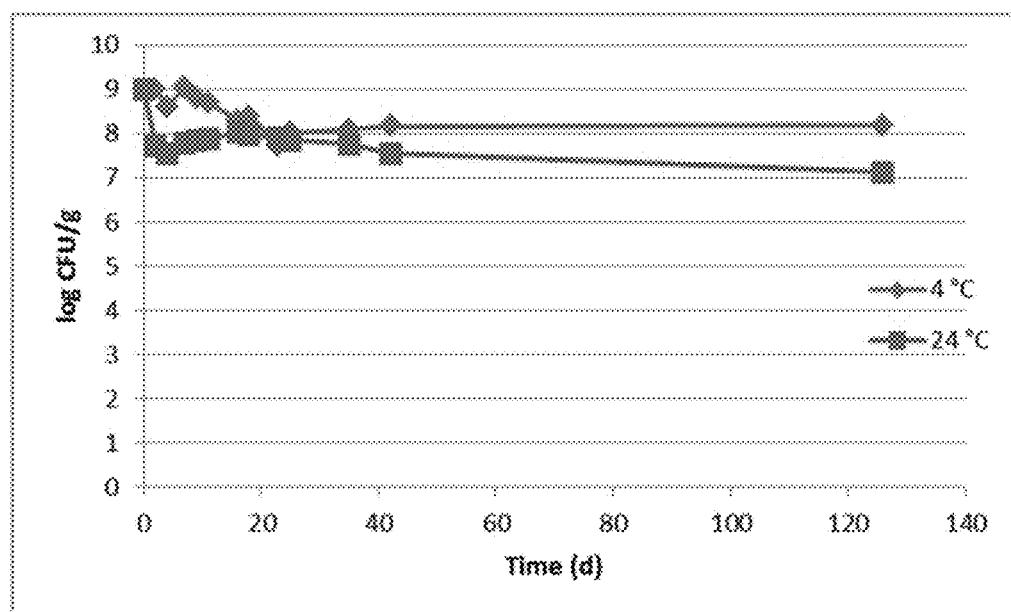
FIG. 2 graphically illustrates that the coated probiotic cells of FIG. 1 maintain viability for extended periods when stored in solution at various temperatures.
Figure 3:
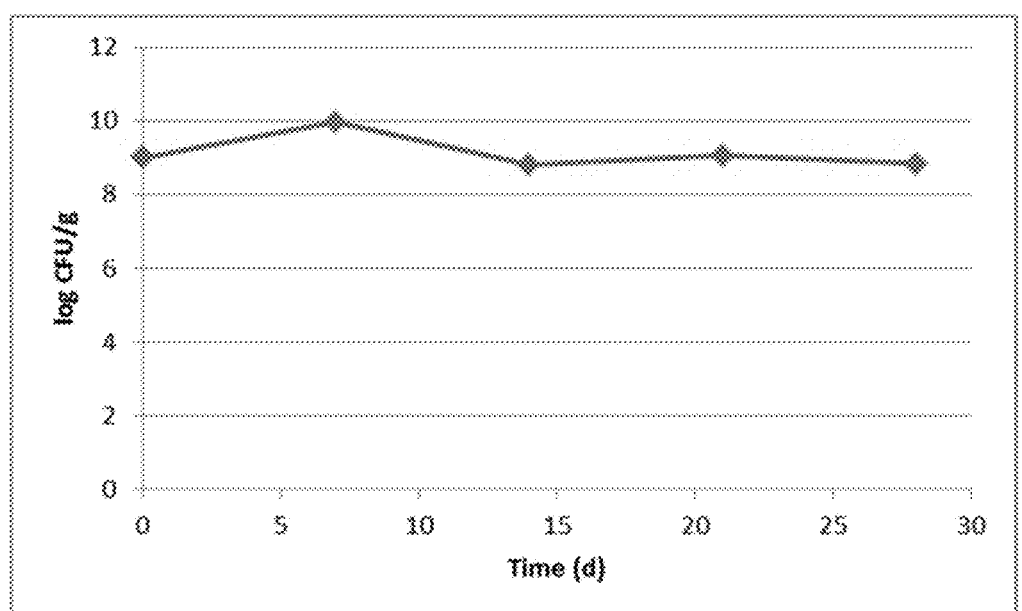
FIG. 3 graphically illustrates the prolonged viability of the coated probiotic cells of FIG. 1 in a dry state.

A method of encapsulating an active agent is provided comprising the steps of: i) applying to the active agent a first hydrophilic swellable coating comprising a sealant film combined with a plasticizer to coat particles of the active agent; and ii) applying to the coated particles a second water-resistant outer coating comprising a hydrophobic non-swellable component combined with an enteric pore former and a plasticizer.

As used herein, the term "active agent" refers to any agent that exhibits therapeutic, nutritive or prophylactic activity on administration to a mammal, including both human and non-human mammals. The active agent may be a biological entity such as peptides/proteins, nucleic acid or living cells including bacterial cells such as probiotic cells, prokaryotic cells, eukaryotic cells, archaebacterial cells, viruses, bacteriophages and the like. The active agent may also be a synthetically prepared entity such as a small molecule, or other synthetically prepared entities including an entity derived from a biological entity such as a peptide, nucleic acid, conjugate compound, etc.

In one embodiment, the active agent is an agent for enteric delivery which may be sensitive to harsh gastric conditions, such as, but not limited to, therapeutic or prophylactic agents such as a probiotic or mixture of probiotics, an anti-inflammatory agent, an anti-cancer agent, an analgesic agent, peptide, nucleic acid-based agent, vaccine, or small molecule. In another embodiment, the active agent is for delivery to the oral cavity, and may similarly include, for example, probiotics or mixtures thereof, and agents to be absorbed by the oral mucosa.

The term "probiotic" refers to live microorganisms that provide health benefits when consumed, for example, by restoring, maintaining or supplementing endogenous microflora. Probiotics, thus, may be used to maintain a healthy microbiome, modulate the immune system, inhibit the growth and activity of harmful bacteria, aid in digestion and support brain function. Probiotics are useful to treat gastrointestinal conditions such as, but not limited to, diarrhea, irritable bowel syndrome, ulcerative colitis, necrotizing enterocolitis, Crohn's disease and infant colic, vaginal infections, urinary tract infections, infection of the digestive tract, *H. pylori* infection, acute respiratory tract infections, as well as conditions that affect oral health. Probiotics include bacteria, yeast and molds. Commonly utilized probiotics belong to the lactic acid bacterial family, e.g. *Lactobacillus, Lactococcus, Enterococcus, Oenococcus, Pediococcus, Streptococcus* and *Leuconostoc* species. Exemplary species of probiotic bacteria include *Lactobacillus* species such as *L. plantarum, L. acidophilus, L. gasseri, L. sakei, L. bulgaricus, L. salivarius, L. casei, L. paracasei, L. rhamnosus, L. delbrueckii* subsp. *bulgaricus, L. brevis, L. johnsonii* and *L.*-ferment; *Streptococcus* species such as *Streptococcus thermophilus; Enterococcus* species such as *Enterococcus faecium*, and *Pediococcus* species such as *Pediococcus acidilactici, Pediococcus pentosaceus, Pediococcus acidilactici* and *Pediococcus halophilus*. Other commonly used probiotics belong to the *Bifidobacterium* genera, such as *B. lactis, B. infantis, B. adolescentis, B. animalis* subsp *animalis, B. animalis* subsp *lactis, B. bifidum, B. longum* and *B. breve*. Probiotics from other genera are also useful including *Escherichia*, e.g. *E. coli, Enterococcus*, e.g. *Enterococcus durans, Bacillus*, e.g. *B. coagulans, B. subtilis, B. cereus, Propionibacterium, Bacteroides, Clostridium, Fusobacterium, Melissococcus, Staphylococcus, Peptostrepococcus, Micrococcus*, Weissella and *Aerococcus*. The probiotic may also be selected from yeasts such as *Saccharomyces*, e.g. *Saccharomyces boulardii, Debaromyces, Candida, Pichia* and *Torulopsis*, and moulds such as *Aspergillus, Rhizopus, Mucor*, and *Penicillium*. Probiotic combinations of two or more microorganisms are also useful.

Active agents that are cells, such as probiotic cells, prokaryotic cells, eukaryotic cells, archaebacterial cells, viruses and bacteriophages, may be dehydrated prior to encapsulation to preserve the cells. Methods such as lyophilization, spray drying, atomization or drying on a fluidized bed may be used for this purpose according to well-established protocols. The preferred method for preparing dehydrated cells is lyophilization.

Lyophilization is a multistep process which involves culturing the cells, suspending them in an aqueous lyophilization medium/buffer, and subjecting them to the freeze drying process. As one of skill in the art will appreciate, the appropriate lyophilization process and medium may differ between cells. Generally, the lyophilization medium comprises a lyoprotectant which protects the cells during the freeze drying process. Lyoprotectants include sugars such as dextrose, sucrose, and trehalose, sugar alcohols such as mannitol, sorbitol, and xylitol, glycine, skimmed milk powder, bovine serum albumin (BSA), polyvinylpyrrolidone (PVP) or combinations thereof. For some cells, a more complicated lyoprotectant is required, such as animal sera. The lyophilization medium will generally also include one or more matrix-forming excipients that function to maintain the shape of the cells during and following freeze drying. Matrix forming additives that may be used include pectin, alginates, PVP, mannitol, BSA, serum, and skim milk. The lyophilization medium may additionally include other additives, such as an antioxidant (e.g. ascorbic acid, citric acid, erythorbic acid, 4-hexylresorcinol, tocopherols, butylated hydroxyanisole, propyl gallate, etc.), or other protective agents such as proteins, amino acids, sugars, and/or carbohydrates. Prebiotics or other nutrients may also be included in the lyophilization medium, including, for example, carbohydrate oligosaccharides such as fructans, e.g. inulin and fructo-oligosaccharide or oligofructose, galacto-oligosaccharides (GOS) (derived from lactose or lactulose), starch or glucose-derived oligosaccharides, e.g. polydextrose, pectic oligosaccharide (derived from pectin), or non-carbohydrate oligosaccharides such as flavanols. Lyophilization of the selected cells is conducted according to standard protocols, for example, the conditions for lyophilizing probiotic cells include condenser temperatures between −50° C. and −80° C. and chamber pressures below 0.120 mbar.

Following preparation of active agents that are cells, these active agents are milled, if required, to form particles having diameters of about 10-400 microns, preferably 50-100 microns. The particles are then coated with a first hydrophilic swellable inner coating comprising a sealant film-forming agent combined with a plasticizer, both of which are consumable. The sealant film provides a continuous, cohesive protective coating that is compatible with the active agent, and preserves stability of the active agent, and viability of active agents which are living cells. The sealant film is combined with a suitable plasticizer to provide flexibility to the coating.

The first hydrophilic swellable inner coating is water soluble when the active agent is cells. Exemplary water-soluble sealant film-forming agents include, but are not limited to, hydroxypropyl methylcellulose, methyl cellulose, sodium carboxymethyl cellulose, hydroxyethyl cellulose, hydroxypropyl cellulose, carboxymethyl cellulose, polyvinyl alcohol, polyvinylpyrrolidone, methacrylic acid polymers, methacrylic acid copolymers, methylmethacrylate copolymer, polyacrylic acid, acrylic acid polymers, acrylic acid copolymers, polyethylene glycol, carrageenan, pullulan, alginates, starch, amylose, whey protein, soy protein, gelatin, and mixtures thereof. Exemplary water-soluble plasticizers include, but are not limited to, glycerin, polyethylene glycols, polyethylene glycol monomethyl ether, propylene glycol, sorbitol, sorbitan, maltitol, mannitol, xylitol, or mixtures thereof. The sealant film-forming agent and plasticizer are combined in an aqueous solvent to form a solution for coating the cell-based active agent.

For water-sensitive active agents such as small molecules and peptides, the hydrophilic, water-swellable coating is soluble and prepared in a non-aqueous (organic) solvent. The term "water-sensitive" is used herein to refer to active agents that are adversely affected by water, for example, active agents which are destabilized, degraded or otherwise adversely affected. These active agents may be prepared through a granulation process with a binding agent in compatible non-aqueous solvents, such as isopropyl alcohol, methanol and ethanol, acetone, tetrahydrofuran, mixtures of dichloromethane with methanol or ethanol, mixtures of acetone and methanol, or mixtures of alcohols, to produce pellets for coating having the desired diameter, e.g. 10-400 microns, preferably 50-100 microns. Examples of suitable hydrophilic, water-swellable film-forming agents which are soluble in an organic solvent include polyvinyl alcohol, polyvinylpyrrolidone methacrylic acid polymers, methacrylic acid copolymers, methyl methacrylate copolymer, polyacrylic acid, acrylic acid polymers, acrylic acid copolymers, polyethylene glycol, zein, cellulose acetate phthalate, cellulose acetate trimellitate, hydroxypropyl methylcellulose, hydroxypropyl methylcellulose phthalate and polyvinyl acetate phthalate. Exemplary plasticizers for use with such film-forming agents (i.e. those which are soluble in an organic solvent) include those which are also soluble in an organic solvent such as, but are not limited to, diethyl phthalate, di-acetylated monoglycerides, tributyrin, triacetin, acetyl tributyl citrate, acetyl triethyl citrate, castor oil, triethyl citrate and dibutyl sebacate Generally, the solution comprising the first coating comprises about 4-15% by wt sealant film-forming agent and about 0.5-3% by wt plasticizer. The sealant film-forming agent is included in the first coating solution in preferred ranges of 5-12% by wt or 6-10% by wt. The first coating solution for active agents, e.g. cells, preferably comprises about 4-10% by wt sealant film-forming agent, preferably 5-8% by wt sealant film-forming agent. The first coating solution for water-sensitive active agents preferably comprises about 8-12% by wt sealant film-forming agent, preferably 9-11% by wt sealant film-forming agent. The plasticizer is included in the first coating solution in a preferred range of 1-2% by wt.

Once coated, the first inner coating of the active agent comprises about 70-100% by wt sealant film-forming agent, preferably 80-90% by wt sealant film-forming agent, and 0-30% by wt plasticizer, preferably 10-20% by wt plasticizer. Preferred ratios of sealant to plasticizer in the first coating are 80:20, 85:15 and 90:10.

Following coating of particles of the active agent with the first inner coating, a second water resistant outer coating is applied to the active agent particles. The outer coating comprises a hydrophobic non-swellable component combined with an enteric polymer and a plasticizer, both of which are consumable.

The hydrophobic component of the second outer coating provides a water-resistant barrier. Examples of suitable hydrophobic non-swellable components for inclusion in the second outer coating include ethylcellulose, fatty acids, waxes and mixtures thereof. Exemplary fatty acids are saturated fatty acids such as stearic acid and palmitic acid. Suitable waxes include animal or vegetable waxes such as beeswax, carnauba wax, paraffin wax, rice bran wax, sunflower wax, jojoba oil wax, sugarcane wax, ouricury wax and polyethylene wax. The hydrophobic component provides water-resistance to the second hydrophobic outer coating, and thus, is present in an amount that renders the second coating to be a water resistant barrier. The hydrophobic component is present in the outer coating in an amount ranging from about 40-80% by weight of the second outer coating, preferably in an amount ranging from 50-60% by weight of the second outer coating.

The enteric polymer prevents dissolution or disintegration of the second outer coating in the acidic gastric environment, but disintegrates at an alkaline pH (e.g. a pH of at least 5.0). Suitable enteric polymers for use in the second outer coating include methacrylic acid copolymers, e.g. methacrylic acid methyl methacrylate copolymers and methacrylic acid ethylacrylate copolymer, cellulose acetate phthalate, cellulose acetate succinate, cellulose acetate trimellitate, hydroxypropyl methylcellulose phthalate, hydroxypropyl methyl cellulose acetate succinate, polyvinyl acetate phthalate, sodium alginate, zein and mixtures thereof. The enteric polymer may be selected to achieve targeted delivery of the active agents. For example, enteric polymers having a lower pKa may be selected to achieve delivery at proximal regions of the small intestine, while enteric polymers having a higher pKa may be suitable for delivery to more distal regions of the intestine. The amount of enteric polymer in the second outer coating is in the range of about 10-40% by weight of the outer coating, preferably in an amount in the range of 20-30% by weight of the outer coating.

The hydrophobic component and enteric polymer are combined with a hydrophobic plasticizer. Examples of such plasticizers include, but are not limited to, diethyl phthalate, di-acetylated monoglycerides, tributyrin, triacetin, acetyl tributyl citrate, acetyl triethyl citrate, castor oil, triethyl citrate and dibutyl sebacate. As one of skill in the art will appreciate, the plasticizer selected may vary with the selected hydrophobic component and enteric polymer. The amount of plasticizer in the outer coating is in the range of about 5-30% by weight, for example, 10-20% by weight of the outer coating.

The selected components of the water-resistant outer coating, including the hydrophobic component, the enteric polymer and the plasticizer, are solubilized in an appropriate solvent for application to the coated active agent particles. The solvent will vary with the enteric polymer utilized in the coating. Examples of solvents include, but are not limited to, alcohols such as isopropyl alcohol, methanol and ethanol, acetone, tetrahydrofuran, mixtures of dichloromethane with methanol or ethanol, mixtures of acetone and methanol, mixtures of alcohols and mixtures of alcohol with water. The components of the second outer coating are combined to form a solution comprising the hydrophobic component in an amount of about 2-10%, preferably 3-8%, the enteric polymer in an amount in the range of about 1-6%, preferably 2-5% and plasticizer in an amount in the range of about 0.1-5%, preferably 1-3%, each by weight of the solution.

The inner and outer coatings are applied to the active agent particles using well-established techniques, e.g. fluidized bed coating at processing temperatures between about 20-45° C. The first inner coating is applied to the particles so as to achieve coverage of the particles, e.g. in an amount that achieves a weight gain of the cells of about 5-10%. Once the target weight gain is reached, the inner coating is dried in a fluidized bed for about 1 hour at 24 degrees C. The second outer coating is then applied to the coated particles so as to render the particles hydrophobic at acidic pH, e.g. a pH less than 5, such as a pH of 3-4. The second outer coating is applied to the coated particles in an amount, for example, that achieves a weight gain of the particles of about 20-60%, for example, 25-50%, or 30-40%. For cells, preferably the outer coating is applied to achieve coverage that results in a weight gain of the coated cells of about 30-60%.

As one of skill in the art will appreciate, the inner and outer coatings may include one or more physiological acceptable additives which do not adversely affect the function of the coatings and/or the integrity or stability of the active agent, including the activity or viability of an active agent which comprises living cells. Exemplary additives include flavouring agents, sweeteners, colouring agents, anti-caking agents, glazing or polishing agents, pH adjusting agents, and preservatives, each in amount in the range of about 0.01-5% by weight of the coating.

Active agent particles coated in accordance with the present methods are protected from moisture, heat and acidity, and advantageously exhibit enhanced stability and/or viability for prolonged periods of time in solution and in a dry state at various temperatures in comparison to active agent which is not coated with the present composite coating. For example, in a dry state, probiotic cells coated with the present composite coating are viable for at least 1 week, preferably, at least 2-3 weeks, and more preferably, at least 1 or more months, at room temperature. Viability periods at temperatures below room temperature are similar or greater. In the liquid state, coated probiotic cells are viable for at least 1 week, preferably, at least 2-3 weeks, at various temperatures ranging from 4-37° C. Increased viability of 1 month or more, e.g. 2, 3, 4 or more months (i.e. 30, 60, 90, 120 or more days) is achieved at room temperature and temperatures below room temperature.

When the present coated active agent is consumed, the water-resistant outer layer protects the cells from the acidic gastric environment. Once exposed to alkaline conditions, such as intestinal fluid, the enteric polymer in the outer layer dissolves and leaches out of the outer layer. This results in hydration and dissolution of the water-soluble inner layer, which in turn advantageously generates osmotic pressure that drives rupture and disintegration of the outer layer, to result in release of the active agent. The present composite coating, thus, provides controlled release of the active agent and enhanced stability/viability of the active agent with the potential for targeted delivery to particular regions of the intestinal tract.

The present coated active agent may also be used to maintain or treat oral health. On oral administration of a coated active agent suitable for this purpose, e.g. a coated probiotic such as S. salivarius, exposure to the alkaline conditions of the oral cavity will result in dissolution of the enteric polymer in the outer layer of the coating, leading to hydration and dissolution of the inner water-soluble layer, followed by rupture and disintegration of the outer layer and release of the probiotic into the oral cavity.

The present coated active agent may be used in conjunction with one or more additional therapeutic or nutraceutical additives. For example, additives which enhance the efficacy of the active agent may be combined with the coated active agent for consumption by an individual to be treated with the active agent. The term "individual" is used herein to refer to both human and non-human mammals. Thus, the present coated active agent is appropriate for veterinary use. Additives may include nutrients such as vitamins, minerals, fibers, fatty acids, amino acids, phytochemicals and the like, or a therapeutic agent such as pain medication, an antacid, anti-fungal, anti-inflammatory, e.g. Non-steroidal Anti-Inflammatory Drug (NSAID), anti-viral and the like. Alternatively, such additives may be combined with the active agent prior to coating, or may be incorporated within the inner or outer coating, so long as the additive does not exhibit a detrimental effect on the function of the inner or outer coating, or on the activity, stability and/or viability of the active agent.

The present coated active agent, including a probiotic o other active agent, may be provided for consumption in liquid form, e.g. in beverages such as juice, flavoured or mineral water or drink, dairy-based beverages, smoothies, protein drinks, and the like, or in liquid or moist foods such as soups, sauces, dairy-based products, e.g. yogurt, cream cheese, cottage cheese, ice cream, prepared meals, baked goods, etc.

The present coated active agent may also be provided in dry form for consumption, formulated for administration in tablet or capsule form, or for addition to liquids, such as water or beverages as above, or for combination with foods, as mentioned above, including cereals, and other dry consumables.

Further, the present coated probiotic cells may be formulated for oral use to treat or maintain oral health. For example, a suitable coated active agent may be suspended in an appropriate liquid, e.g. water or saline, for use as an oral rinse. Alternatively, the coated active agent may be formulated into a paste or gel for oral administration. Flavouring agents may also be included in such formulations as well as mouth fresheners such as menthol.

Embodiments of the invention are described by reference to the following specific examples which are not to be construed as limiting.

Example 1—Probiotic Encapsulation

A composite coating was applied to probiotic cells using the following methods.

Encapsulation and lyophilization of probiotic powder—a precursor solution of pectin, trehalose, sodium ascorbate, and phosphate buffers was prepared by dissolving the excipients shown in Table 1 in water. Prior to lyophilization, liquid de Man, Rogosa and Sharpe culture media (MRS broth) comprising *Lactobacillus casei* cells (with an initial optical density (OD) of 0.91) was added to the precursor solution and homogeneously mixed to produce a probiotic polymer suspension. The probiotic suspension was then frozen at −80° C. for 24 hours and lyophilized at a condenser temperature of −80° C. and a chamber pressure of 0.1 mbar until dried.

TABLE 1

Composition of probiotic polymer solution

| Materials | Function | Concentration (% w/w) | Conc'n Range (% w/w) |
|---|---|---|---|
| Pectin | Filler/Prebiotic | 1.7% | 1.7% |
| Trehalose | Lyoprotectant/ Osmoprotectant | 5.2% | 4.6-10.2% |
| Sodium ascorbate | Antioxidant | 5.2% | 4.6-10.2% |
| Sodium phosphate dibasic | Buffer/ Lyoprotectant | 0.6% | 0.6% |

TABLE 1-continued

Composition of probiotic polymer solution

| Materials | Function | Concentration (% w/w) | Conc'n Range (% w/w) |
|---|---|---|---|
| Sodium phosphate monobasic | Buffer/Lyoprotectant | 0.1% | 0.1% |
| Lactobacillus casei | Cells | 4.4% | 4.4% |
| Water | Solvent | 82.7% | 72.8-84.0% |

Application to probiotic powder of inner and outer polymer coatings—two polymer coatings were applied onto the lyophilized probiotic powder using a fluid bed coater. The polymer solutions for the inner coating and the outer coating were prepared according to Tables 2 and 3, respectively. The two polymer solutions were coated onto the capsules with a top spray nozzle. Target weight gains for inner and outer coating were 5% and 30%, respectively.

TABLE 2

Composition of inner coating polymer solution

| Materials | Function | Concentration (% w/w) | Conc'n Range (% w/w) |
|---|---|---|---|
| Hydroxypropyl methycellulose | Seal coating/disintegrant | 7.3% | 4.9-7.8% |
| Polyethylene glycol 300 | Water-soluble plasticizer | 1% | 1%-2% |
| Water | Solvent | 92.6% | 91-94% |

TABLE 3

Composition of outer coating polymer solution

| Materials | Function | Concentration (% w/w) | Conc'n Range (% w/w) |
|---|---|---|---|
| Ethylcellulose | Water-resistant barrier | 6.0% | 4.7-6.0% |
| Methacrylic acid-methyl methacrylate copolymer | Enteric pore former | 2.6% | 2.6-3.9% |
| Dibutyl sebacate | Hydrophobic plasticizer | 1.7% | 1.5-2% |
| Isopropyl alcohol | Solvent | 71.8% | 61.3-77.1% |
| Water | Solvent | 17.9% | 14.1-26.8% |

Storage Conditions

The coated powders were placed in water with pH value of 3 at 4 and 24° C. to assess the resistance of the coatings to water at different temperatures. Additionally, dry coated powders at 24° C. were also tested.

Probiotic Cell Viability Testing

Coated powder samples were tested for their cell viability at predetermined time points. The samples were first degraded in phosphate buffer saline (pH 7.4) for 1 hour. The samples were then diluted and plated on MRS agar culture and enumerated at 37° C. The numbers of colony-forming units of each sample were counted to determine cell viability.

Results

The loss of probiotic cell viability after the lyophilization and coating processes was minimal, indicating that the cells endured these processes very well.

Coated probiotic powders stored in liquid at 4° C. (diamonds) exhibited 1 log reduction in colony forming units (CFU)/gram over 126 days. Coated probiotic powders stored in liquid at 24° C. (squares) exhibited 1 log reduction over 25 days and 2 log reduction over 126 days. These results surpass the probiotic viability achieved with other microencapsulation technologies.

Furthermore, coated probiotic powders kept in a dry state at 24° C. remained stable with negligible loss in cell viability for at least 25 days.

Example 2—Small Molecule Encapsulation

A composite coating is applied to vitamin C (ascorbic acid), a water-sensitive small molecule active agent, using the following methods.

Granulation of ascorbic acid—granulated pellets of ascorbic acid are prepared by dry compaction of a mixture of ascorbic acid and polyvinylpyrrolidone as a binding agent as listed in Table 4. The homogeneous mixture is compacted in its dry form and then sieved through appropriate mesh sizes to obtain the required particle sizes (50-100 um).

TABLE 4

Composition of granulation mixture

| Materials | Function | Concentration (% w/w) | Conc'n Range (% w/w) |
|---|---|---|---|
| Ascorbic Acid | Active agent | 96% | 90-97% |
| Polyvinylpyrrolidone | Lyoprotectant/Osmoprotectant | 4% | 3-10% |

Application to granulated ascorbic acid pellets of inner and outer polymer coatings—Two polymer coatings are applied onto the granulated ascorbic acid pellets using a fluid bed coater. The polymer solutions for the inner coating and the outer coating are prepared according to Tables 5 and 6, respectively. The two polymer solutions are coated onto the pellets with a top spray nozzle. Target weight gains for the inner and outer coating are 10% and 60%, respectively.

TABLE 5

Composition of inner coating polymer solution

| Materials | Function | Concentration (% w/w) | Conc'n Range (% w/w) |
|---|---|---|---|
| Polyvinylpyrrolidone | Seal coating/disintegrant | 10% | 6-12% |
| Triethyl citrate | Plasticizer | 1.5% | 1%-2% |
| Isopropyl alcohol | Solvent | 88.5% | 86-93% |

TABLE 6

Composition of outer coating polymer solution

| Materials | Function | Concentration (% w/w) | Conc'n Range (% w/w) |
|---|---|---|---|
| Ethylcellulose | Water-resistant barrier | 6.0% | 4.7-6.0% |
| Methacrylic acid-methyl methacrylate copolymer | Enteric pore former | 2.6% | 2.6-3.9% |
| Dibutyl sebacate | Hydrophobic plasticizer | 1.7% | 1.5-2% |
| Isopropyl alcohol | Solvent | 71.8% | 61.3-77.1% |
| Water | Solvent | 17.9% | 14.1-26.8% |

The invention claimed is:

1. A composition comprising a probiotic encapsulated with a composite coating, wherein said composite coating comprises:
   i) a first hydrophilic water-swellable inner coating comprising i) 80-90% by weight of a sealant film-forming agent selected from the group consisting of hydroxypropyl methylcellulose, methyl cellulose, sodium carboxymethyl cellulose, carboxymethyl cellulose, starch, amylose, whey protein, soy protein, gelatin, and mixtures thereof and ii) 10-20% by weight of a water-soluble plasticizer selected from the group consisting of glycerin, polyethylene glycol, propylene glycol, sorbitol, sorbitan and mixtures thereof, wherein said first hydrophilic water-swellable inner coating is applied to particles of the probiotic; and
   ii) a second water-resistant outer coating comprising 40-80% by weight of a hydrophobic non-swellable component selected from the group consisting of ethylcellulose, beeswax, carnauba wax, rice bran wax, sunflower wax, jojoba oil wax and mixtures thereof, 10-40% by weight of an enteric polymer which disintegrates at a pH of at least 5.0 and is selected from the group consisting of methacrylic acid copolymers, cellulose acetate succinate, hydroxypropyl methylcellulose acetate succinate, polyvinyl acetate phthalate, sodium alginate, zein and mixtures thereof, and 10-20% by weight of a hydrophobic plasticizer selected from group consisting of castor oil, dibutyl sebacate and mixtures thereof,
   wherein said second water-resistant outer coating is applied to the first hydrophilic water-swellable inner coating; and
   wherein the composite coating protects the probiotic during storage in an acidic environment for at least one week.

2. The composition of claim 1, wherein the hydrophobic non-swellable component comprises 50-60% by weight, and the enteric polymer comprises 20-30% by weight of the second outer coating.

3. The composition of claim 1, wherein the second outer coating comprises ethylcellulose as the hydrophobic non-swellable component, methacrylic acid-methyl methacrylate copolymer as the enteric polymer, and dibutyl sebacate as the hydrophobic plasticizer, and the first inner coating comprises hydropropyl methylcellulose as the sealant film-forming agent (polymer) and polyethylene glycol as the plasticizer.

4. The composition of claim 1, wherein the hydrophobic non-swellable component is water-resistant with a melting point in the range of 45–85° C.

5. The composition of claim 1, wherein the active agent is living cells.

6. A method of preparing a composition comprising a probiotic encapsulated in a composite coating as defined in claim 1 comprising the steps of:
   i) applying to particles of the probiotic the first hydrophilic water-swellable inner coating to coat the particles;
   ii) applying to the coated particles the second water-resistant outer coating; and
   iii) formulating the coated particles to form a dry or liquid composition.

7. The method of claim 6, comprising a step of preparing the first hydrophilic water-swellable inner coating solution comprising 4-15% by weight of the sealant and 0.05-0.5% by weight of the plasticizer.

8. The method of claim 6, comprising a step of preparing the second water-resistant outer coating solution comprising about 2-10% by weight of the hydrophobic non-swellable component, about 1-10% by weight of the enteric polymer, and about 0.1-5% by weight of the plasticizer.

9. The method of claim 6, wherein the first inner coating is applied to the particles of probiotic in an amount that achieves a weight gain of the probiotic particles of about 5-10%, and the second outer coating is applied to the coated probiotic particles in an amount that achieves a weight gain of the coated probiotic particles of about 20-60%.

* * * * *